United States Patent [19]

Cheslak

[11] Patent Number: 4,790,752
[45] Date of Patent: Dec. 13, 1988

[54] ILLUMINATED DENTAL IMPRESSION TRAY

[75] Inventor: Leonard W. Cheslak, Tustin, Calif.

[73] Assignee: Poly-Optical Products, Inc., Santa Ana, Calif.

[21] Appl. No.: 115,668

[22] Filed: Nov. 2, 1987

Related U.S. Application Data

[63] Continuation-in-part of Ser. No. 9,413, Jan. 30, 1987, Pat. No. 4,765,701.

[51] Int. Cl.$^4$ ............................................... A61C 9/00
[52] U.S. Cl. ...................................... 433/37; 433/229
[58] Field of Search .................. 433/148, 149, 37, 229

[56] References Cited

U.S. PATENT DOCUMENTS 4,553,936 11/1985 Wang ..................................... 433/37
4,631,030 12/1986 Weissenfluh ......................... 433/149

Primary Examiner—Robert Peshock
Attorney, Agent, or Firm—Nilsson, Robbins, Dalgarn, Berliner, Carson & Wurst

[57] ABSTRACT

A dental impression tray constructed from an optically transmissive material prepared with appropriately positioned recesses to direct light towards a U-shaped channel formed in the body of the tray. The channel is dimensioned to receive a portion of a patient's teeth. The recesses are formed in the outermost surfaces of the dental tray sides. In particular, multiple, spaced-apart recesses are formed in the outermost surfaces of the tray sides to deflect light into the channel area, which may have deposited therein a light polymerizable or curable material. Light is introduced into the tray through at least a first light portal which is integrally formed in a side of the tray.

23 Claims, 3 Drawing Sheets

ILLUMINATED DENTAL IMPRESSION TRAY

RELATED CASES

This application is a continuation-in-part of U.S. patent application Ser. No. 009,412, filed on Jan. 30, 1987, now U.S. Pat. No. 4,765,701 issued 8/23/88 in the name of Leonard W. Cheslak, and assigned to the same assignee as the instant application.

BACKGROUND OF THE INVENTION

The present invention is directed to the art of optically transmissive bodies, specifically to an optically transmissive dental impression tray.

Optically transmissive bodies, including both filamentous and other body types have found use in many applications. One particular application for which optically transmissive bodies have been used is in the transmission of light, i.e. as an illuminator.

An illuminator is a device where the light, which is normally traversing longitudinally through the optically transmissive body, is diverted laterally outward from the body at various points to illuminate given areas. Illuminators are formed by modifying an optically transmissive body to emit an incremental amount of the light outward from discrete portions of the body. Thus by using only a single light source, i.e., a bulb, numerous points of light can be obtained using an optically transmissive body prepared to emit light in this manner.

There are numerous methods by which an optically transmissive body can be prepared to emit light from discrete portions. For example, the optically transmissive body can be cut with grooves at various points along its length, with one or more of the groove surfaces coated with a reflective material. This reflective material will reflect any light which impinges upon it. By properly positioning the grooved surfaces light can be directed outward from any desired position along the body.

Mirrors angularly embedded in or laid along the optically transmissive body can be substituted for the reflectively coated groove surfaces. Optically transmissive bodies modified in this manner will transmit light in a similar manner as the light impinges upon the mirrored surfaces.

Examples of optical illuminators prepared by the discussed techniques are generally disclosed in U.S. Pat. Nos. 4,052,120 issued to Sick et al.; 4,173,390 issued to Kach; and 4,196,962 issued to Sick.

Another example of an optical illuminator is where a optically transmissive body is coated along a portion of its peripheral surface with an illuminant material. This illuminant material functions as a secondary light source by either radiating or reflecting light. By properly positioning this coating the light can be emitted in any direction from out of the body. A fiber optic illuminator prepared by this technique is disclosed in U.S. Pat. No. 4,128,332 issued to Rowe.

Another technique of modifying a optically transmissive body to cause the emission of light involves roughening a portion of the peripheral surface of the optically transmissive body. The light will pass out through this roughened surface. A fiber optic prepared in this manner is disclosed in U.S. Pat. No. 3,829,675.

Optically transmissive bodies have also been prepared, as disclosed in U.S. Pat. No. 4,172,631 issued to Yevick, to possess spaced apart longitudinal reflecting surfaces. As disclosed in Yevick, optic fibers which have been formed with grooves are laid upon a rigid reflective material, which possess ridges formed to be compatible with the grooves of the fiber. The finished product thus includes a multiplicity of mirrored surfaces positioned along the length of the fibers. The height or depth of these surfaces are specifically calculated to radially inwardly reflect an incrementally increasing quantity of the total light passing through the fiber. This light will pass across and through the opposite side of the fiber.

While optical illuminators prepared by the discussed techniques emit some of the light passing therethrough the degree of light emitted is not always adequate for an intended purpose. Further these discussed methods of preparing optical illuminating devices are generally costly. That is, the cost of imbedding mirrors into a optically transmissive body, or of coating previously provided grooved surfaces for certain applications is cost prohibitive.

A recent application of the technology for preparing optically transmissive bodies is in the field of dental impression trays. A particular type of optically transmissive dental tray is disclosed in U.S. Pat. No. 4,553,936, issued to Wang on Nov. 19, 1985. The dental tray disclosed in this patent transmitts actinic light to a channel formed in the tray which can hold a light polymerizable material. The disclosed material is cured by light activated polymerization.

While the dental tray disclosed in the Wang patent is useful for preparing a dental impression using a light polymerizable material, the amount of light transmitted to the channel for affecting this polymerization varies and is not evenly distributed throughout the tray channel. Thus the material is unevenly polymerized. It is thus apparant that the useability of an optically transmissive dental tray for preparing dental impressions is dependent upon the optical illuminating properties of the tray. The technology disclosed in the Wang patent does not add to the technology of preparing an illuminating optically transmissive body previously discussed, but merely applies this technology in preparing dental impression trays.

SUMMARY OF THE INVENTION

The present invention is directed to optically transmissive bodies which are formed with at least one recess at a defined location in a side of the body. Each recess is defined by two opposing surfaces which angle inwardly toward each other. Light which impinges upon these inwardly angling surfaces is deflected. Some of the light deflected in this manner will pass out through the opposing side of the body, provided such side is not coated by a nontransparent material.

By the appropriate placement of numerous recesses the light can be outwardly emitted from more than one intended location along the length of the body. Furthermore, by forming a series of spaced apart, but contiguous recesses, an increased amount of light can emitted from the body.

One particularly advantageous use of the invention is in the preparation of a dental impression tray. Specifically, a dental tray prepared in accordance with the invention is constructed from an optically transmissive material prepared with appropriately positioned recesses to direct light towards a U-shaped channel formed in the body of the tray. The channel is dimensioned to receive a portion of a patient's teeth. The recesses are formed in the outermost surfaces of the dental tray sides. In particular, multiple, spaced-apart recesses are formed in the outermost surfaces of the tray sides to deflect light into the channel area. Light is introduced into the tray through at least a first light portal which is integrally formed in a side of the tray.

The method of using the dental tray for preparing a dental impression of a patient's teeth involves depositing a light curable or polymerizable material in the channel. The dental tray is then inserted into the patient's mouth with the selected teeth embedded into the material. A light source is then directed onto the light portal. Light enters the dental tray interior through the portal and passes through the tray body. Light impinging upon each recess surface is deflected in an opposing direction, and when properly situated these recess surfaces direct the light towards the channel. As the light enters the channel the initiation of the polymerization or curing of the material occurs. A finished dental impression is removed from the channel after the material is completely cured or polymerized.

DESCRIPTION OF THE DRAWINGS

The present invention may be better understood, and its numerous objectives will become apparent, from the following figures, wherein like reference numerals refer to like elements in the several figures and wherein.

DESCRIPTION OF THE INVENTION

The present invention is directed at optically transmissive bodies, which bodies have the characteristic of total internal reflection and are formed with one or more recesses. Each of these recesses is defined by two opposing surfaces which angle inwardly toward each other. A portion of the light traveling through the optically transmissive body is deflected by these surfaces in a direction to be emitted through the opposing side of the body.

Figure 1:
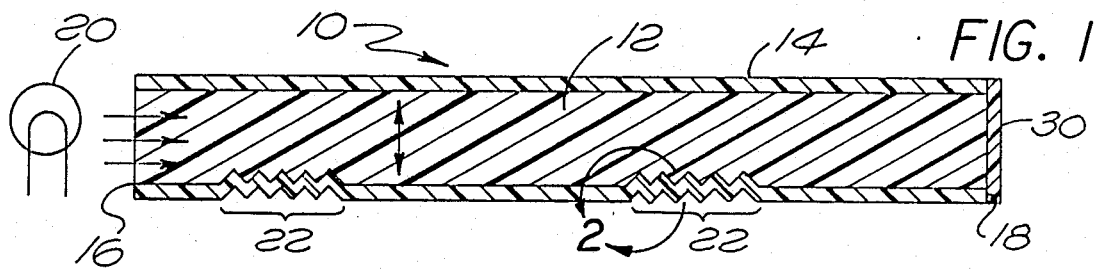
FIG. 1 is a lengthwise cross-sectional view of a fiber optic illuminator in accordance an embodiment of the invention.

Referring to FIG. 1, one embodiment of an optically transmissive body is illustrated. This body is in the form of an illuminator as seen generally at 10. It should be noted that while the illuminator 10 illustrated in FIG. 1 is formed from a optically transmissive fiber, that is, a fiber characterized by total internal reflection, the optically transmissive body from which the illuminator of the invention may be formed includes any desired shape, e.g., filamentous or rectangular. The only requirement is that the material from which the body is prepared is the type of material which will provide that light can be directed through the length of the body by substantially total internal reflection.

Generally, the types of materials from which optically transmissive bodies useful for the purposes of the invention can be prepared are well known in the art. These materials will be those which allow for the transmission of light but have a refractive index greater than the refractive index of air. More expensive materials include various types of glass, while other materials include various types of acrylics and polystyrenes.

Typically, non-filamentous bodies will be constructed from a single material characterized by a refractive index which allows for the internal reflection to occur at the boundary of that material and the surrounding air. Fibrous optically transmissive bodies may be prepared in this manner but may also be formed to have a core prepared from a material having a first refractive index, which core is enveloped by another material having a second refractive index. By providing that the material forming the core is of a greater refractive index, the desired internal reflection of light is obtained.

As seen in FIG. 1, the fibrous illuminator 10 is formed with an internal core 12 of material which is substantially transparent and has a first refractive index. This transparent core 12 is substantially sheathed by an outer cladding 14 of a substantially transparent material having a second refractive index. The internal reflection is provided by insuring that the refractive index of the cladding 14 material is less than the refractive index of the core 12 material.

The optical fiber illuminator 10 has first and second ends 16 and 18, with end 16 being illuminated by a light source 20. The light source 20, which may be an incandescent bulb, may be used to illuminate the end 16 of more than one illuminator 10. This would increase the efficiency of the use of the particular light source 20.

The light will pass through the end 16 and travel through the core 12 in accordance with known principles of internal reflection, i.e., Snell's law. In accordance with Snell's law, a substantial portion of the light traveling through the core 12 will be angularly deflected across the core 12 at the interface between the core 12 and the outer cladding 14. It is further believed that if the light is directed at this interface at other than within a prescribed range of angles, the light will pass through the outer cladding 14. It is this general principle of which the invention makes use; however, since this is only a theory, the present invention should not be bound or limited in any manner by it.

The illuminator 10 of the invention is formed with one or more recesses 24, with the recesses 24 of the illustrated embodiment being arranged as a series of recesses 24 contained in a defined region, with one such region generally indicated at 22. The recesses 24 which form the region 22 are defined by two opposing surfaces 26 and 28 which angle inwardly toward the fiber optic to define an included angle therebetween which, as will be discussed further herein, is such to cause the deflection of light toward the opposing side of the illuminator 10. This deflection occurs at the interface between the core 12 and the cladding 14; however, it is to be understood that an illuminator prepared from a fiber optic comprised of a single material will allow for this deflection at the interface between the material and the surrounding air.

Thus, each of the recess 24 of the regions 22 function to cause an emission of light out from the opposing side of the illuminator 10. By utilizing more than one recess 24 to form a recess region 22, a larger amount of light is directed out of the illuminator. Depending on the amount of light which is desired to be emitted in this manner, a single recess may be formed in the fiber optic, or numerous recesses 24 may be formed at spaced apart locations.

The individual recesses 24 of the defined region 22 are preferably formed in a manner to insure that when the fiber optic being used to construct the illuminator 10 includes an outer cladding 14 that this outer cladding 14 remains intact. That is, the manner by which the individual recesses 24 are formed should insure the integrity of the cladding 14. Methods useful for manufacturing the optical illuminator 10 of the invention in this manner include, but are not limited to, the various cast molding processes or injection molding process, whereby an optical fiber is continuously molded with one or more of the defined regions 22 of recesses 24 being formed during the molding process, or by a hot or cold embossing method where the individual recesses 24 are formed by deforming the surface of a virgin fiber optical rod at desired locations.

When preparing the individual recesses 24 by one of these methods or any equivalent method, the material of the fiber optic will flow somewhat after the recess 24 is formed. The result is that the recesses 24, which are generally rectangular, are shaped to have their various corners rounded off, as seen better in FIG. 2. As will be described in greater detail below, other methods may be used to form the individual recesses 24, e.g., machine cutting the optic fiber, with the resulting recess 24 having a more pronounced rectangular shape, as better seen in FIG. 3.

Figure 2:
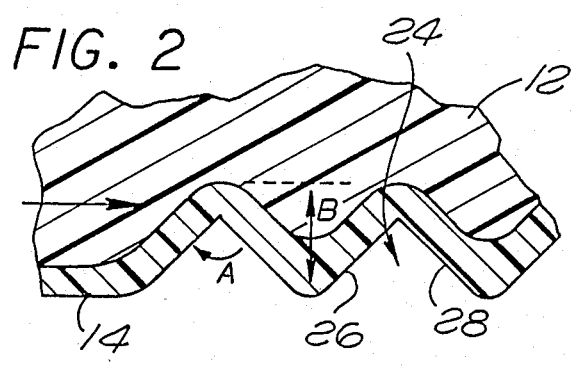
FIG. 2 is an enlarged portion of FIG. 1 at line 2.

While the individual recesses 24 may be spatially separated in the surface of the illuminator 10, even when arranged within a defined region 22 in accordance with a preferred embodiment, the individual recesses 24 are arranged contiguous to each other, as best seen in FIGS. 1 and 2. This manner of contiguously positioning the individual recesses 24 maximizes the illumination which will pass out of the opposing side of the illuminator 10.

Referring specifically to FIG. 2, an individual recess 24 in accordance with an embodiment of the invention will be described in greater detail. These recesses 24 are defined by two opposing surfaces 26 and 28 which angle inwardly to define an "included" angle A therebetween, which angle A is generally from about seventy degrees to about one hundred ten degrees, more preferably from about eighty-five to about ninety-five degrees. By forming the surfaces 26 and 28 at this angle A, light which impinges on either one of these surface 26 or 28 will be deflected toward and through the opposing side of the illuminator 10, provided that such side is not coated with an opaque material. If an opaque covered fiber optic is used, such coating must be removed in order to allow for the emission of the light.

The depth of the individual recesses 24 is not critical to the invention, that is, the individual recesses 24 do not have to be deep in comparison to the diameter of the optical fiber, or for that matter, any optically transmissive body, in order to function in accordance with the invention. Generally the depth, indicated by the Arrow B, of the individual recesses 24 may vary from about two to about eighty percent of the cross-sectional distance of the fiber optic, as indicated by the Arrow C in FIG. 1, or for that matter the cross-sectional distance of any shaped body forming an illuminator in accordance with the invention.

As stated, this distance is not critical, since it has been found that the amount of light deflected will not significantly differ with varying recess depths. However, the depth of the recess 24 will affect the amount of light which will continue to pass through the illuminator 10, with the amount of light diminishing as the depth of the recess 24 increases. Thus, it is preferable to provide the recesses 24 with depths of from about two to about twenty-six percent of the cross-sectional distance, more preferably from about two to about sixteen percent.

By way of example, recesses of varying "included angles" and varying "depths" were formed in optical fibers having diameters of three sixteenths (3/16) of an inch. These fibers were of the type having an acrylic inner core and a styrene outer cladding. Light from a three candle power incandescent bulb was directed through the prepared fiber optic illuminators. The amount of light which was emitted out through the various recesses was measured, with good illumination, between one hundred and two hundred foot lamberts being demonstrated for recesses of varying depths, that is, recesses having depths of from 0.005" to 0.15", which is substantially equivalent to a depth of from about two to about eighty percent of the cross-sectional distance of the fiber.

However, good illumination, again between one hundred and two hundred foot lamberts, was found only with those recesses having an included angle of from seventy to one hundred ten degrees, with even better illumination, that is, closer to two hundred foot lamberts, found for recesses having an included angle of from eighty-five to ninety-five degrees.

Figure 3:
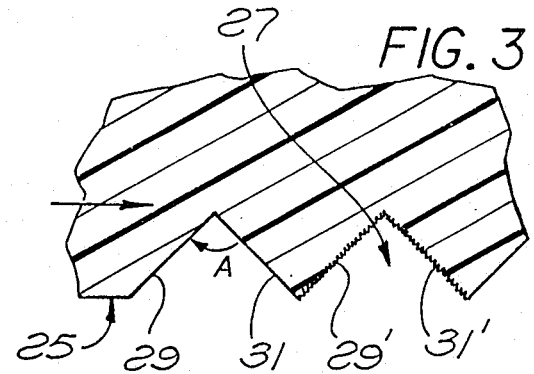
FIG. 3 is an enlarged cross-sectional view of a series of recesses formed in a fiber optic illuminator in accordance with another embodiment of the invention.

Referring now to FIG. 3, a differently configured recess 27 in accordance with another embodiment of the invention will be described. This recess 27, which is formed in an illuminator 25, is also defined by two opposing surfaces 29 and 31 which angle inwardly toward each other. However, the recess 27 of this embodiment is formed by machine cutting, and as a result possesses sharper edges and corners than the recess 24 previously described. This type of recess 27, when formed in a virgin fiber optic having an outer cladding, will not retain the cladding as illustrated for the recess 24. Further, while both recesses 24 and 27 provide ample illumination for the purposes of the invention, by forming the recess with a more rounded internal apex, that is, the top of the recess inside the illuminator as seen in FIG. 2, the illumination obtained is greater. The reason for this effect is believed to result from more light being deflected from the rounded sloped surface of the recess 24, as compared to the generally straight surface of the recess 27; however, this is merely a theory and is not to be construed to limit the scope of the invention.

In order to increase the illuminating characteristic of the recesses described herein, it is preferable to texturize one or both of the recesses' surfaces, with surfaces 29' and 31' of the recess 27' being illustrated as texturized in FIG. 3. This texturization increases the quantity of light which passes through the respective surface. The surfaces can be texturized by any suitable process, e.g., machining or sanding.

Figure 4:
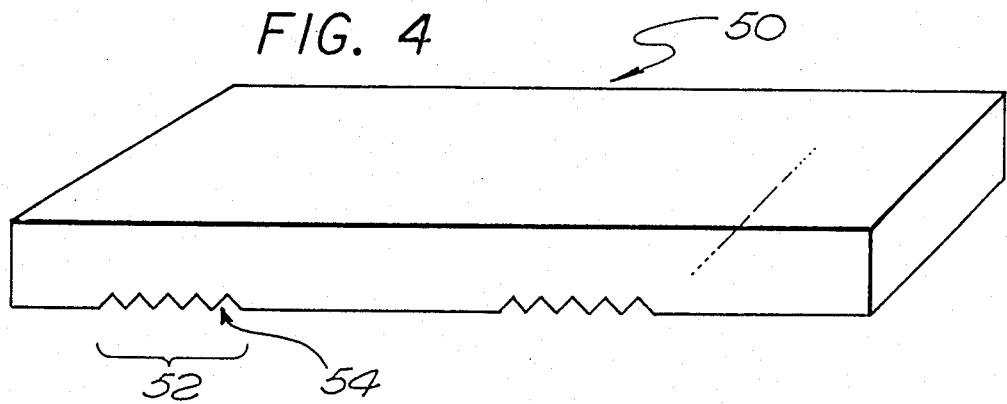
FIG. 4 is a perspective view of an illuminator in accordance with another embodiment of the invention, formed from a generally rectangular optically transmissive body.
Figure 5:
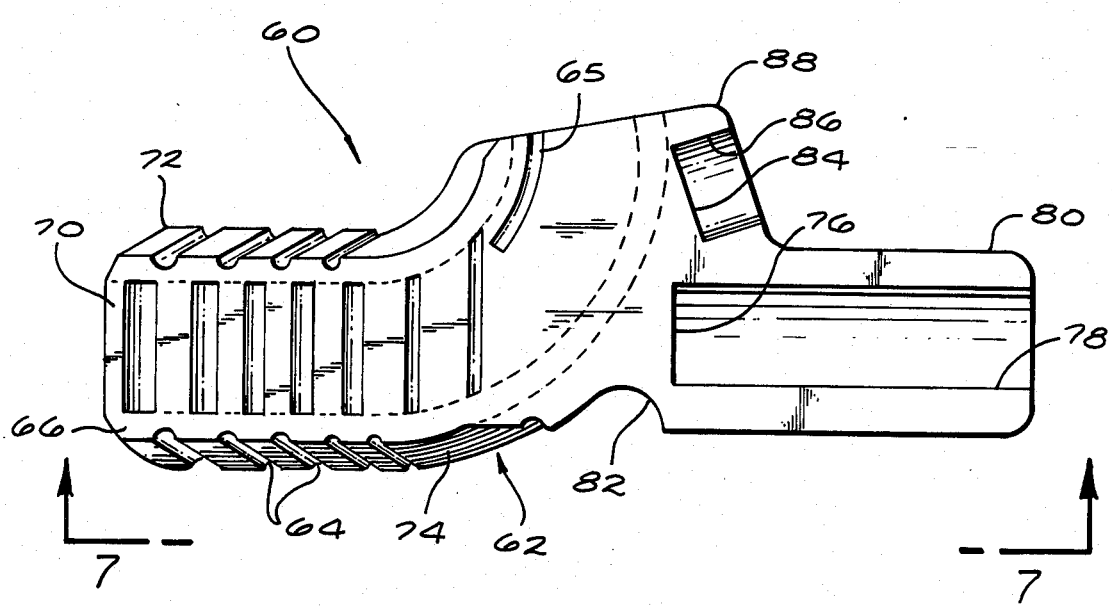
FIG. 5 is a bottom view of an optically transmissive dental tray in accordance with an embodiment of the invention.
Figure 7:
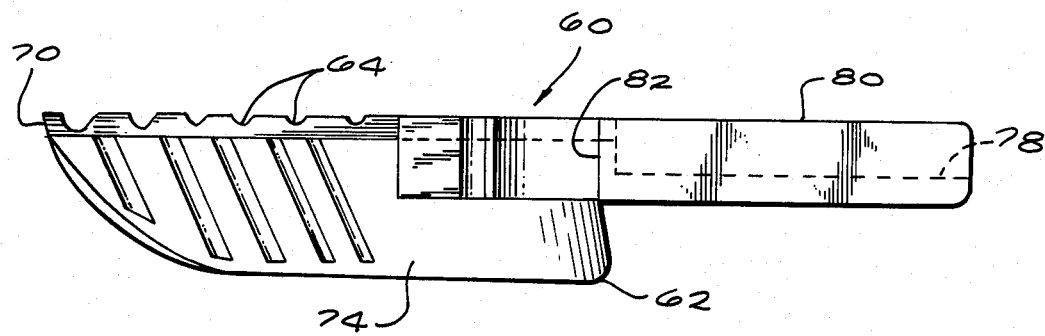
FIGS. 7 and 8 are side views of the dental tray of FIG. 5.
Figure 6:
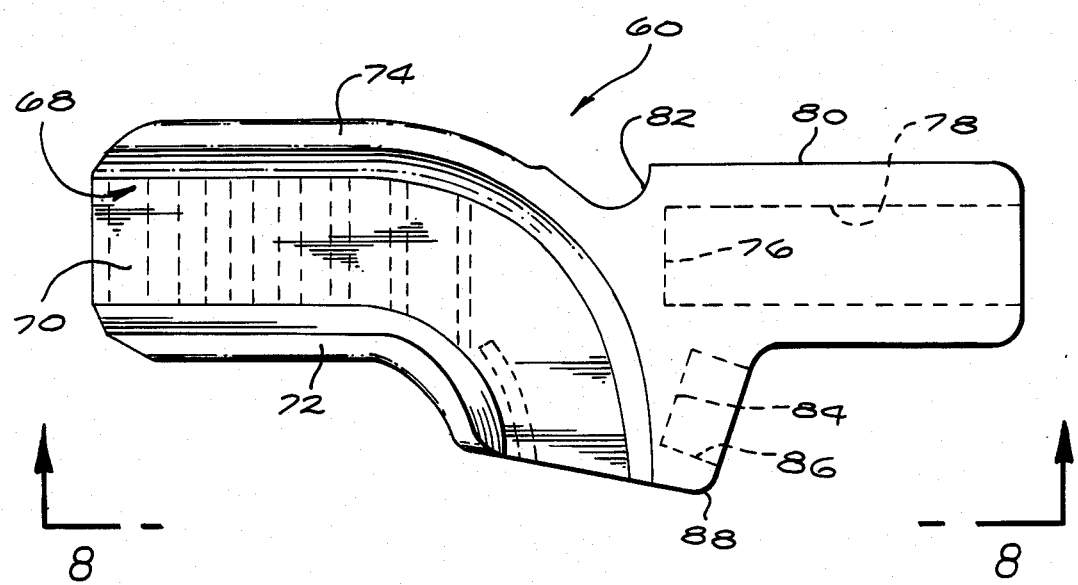
FIG. 6 is a top view of the dental tray of FIG. 5.
Figure 8:
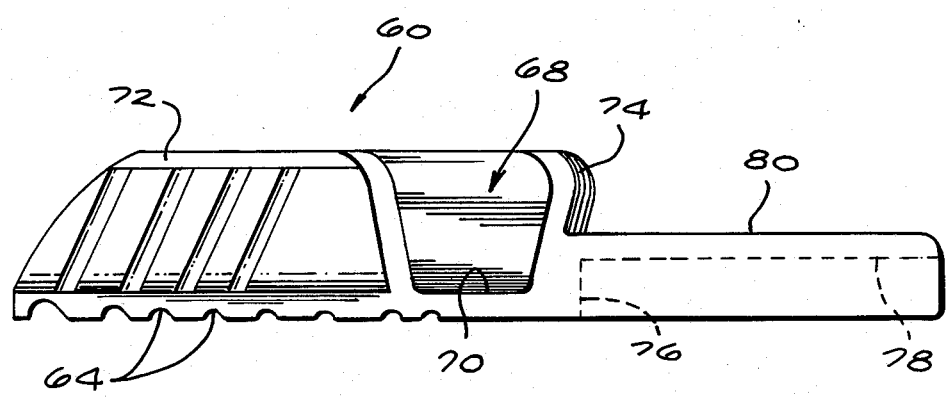

While both of the embodiments illustrated in FIGS. 1, 2 and 3, are of illuminators prepared from filamentous bodies, as stated, other optically transmissive bodies may be used to form an illuminator in accordance with the invention. FIG. 4 illustrates an illuminator seen generally at 50 prepared from a rectangular shaped body of a material which, while transparent to light has a refractive index such that light will travel by substantially internal reflection therethrough. Examples of suitable materials include but are not limited to acrylics and styrenes, polymers and certain types of glass. This illuminator 50 is formed with a first region 52 of individual recesses 54. The recesses 54 are individually formed in a manner similar to the manner by which the recesses 27 are formed, that is, the recesses 54 are formed by machine cutting. Thus the recesses 54 will resemble in appearance the recesses 27.

In order to insure that light will travel in both directions through any optically transmissive body an illumination source should be positioned along various portions of the body. In accordance with the embodiments illustrated in FIGS. 1–4 the illumination source is positioned at opposing ends of the body, such as at the ends 16 and 18 of the illuminator 10 illustrated in FIG. 1.

While a second light source such as an incandescent bulb may be positioned proximate both ends 16 and 18, it is preferable if a coating 30 of an illuminant material is applied to the end 18. This material will absorb and become illuminated by any light passing through the end 18. This coating is preferably white and may either be a white paint or a white polymeric material applied to the end 18. As the light passes through the end 18 this white coating is illuminated and functions as a secondary light source to redirect any light which would normally pass out of the end 18 back through the illuminator 10. An illuminator prepared in this manner will possess increased efficiency.

Referring now to FIGS. 5–8, an optically transmissive dental tray prepared in accordance with an embodiment of the invention will now be discussed. As stated above, an optically transmissive body prepared in accordance with the invention is constructed from a material which allows for the transmission of light, but has a refractive index greater than the refractive index of air. Examples of such materials include various types of glass, acrylics and polystyrenes.

In particular, the dental tray of the invention, as seen generally at 60, is generally a trough-shaped body 62 formed from a material as discussed above which has the characteristic of total internal reflection. The trough-shaped body 62 defines a channel 68 which traverses the length of the dental tray 60. The dental tray 60 is formed with one or more recesses, as seen generally at 64. Each of these recesses 64 are similar in form to the recesses 24 described above for the embodiment illustrated in FIGS. 1 and 2. As stated, each recess 24, and for this embodiment recesses 64, are defined by two opposing surfaces which angle inwardly toward each other, preferably to define an included angle. A portion of the light traveling through the optically transmissive body 62 is deflected by these surfaces. A portion of the deflected light is emitted through the opposing surface of the body 62, which is in effect the surfaces of the dental tray forming the channel 68.

It should further be noted that the various angular relationships between the surfaces of the recesses 64 are the same as described above for the recesses 24. These recesses 64 may also be formed in accordance with the various methods discussed above for forming the recesses 24 illustrated in FIGS. 1 and 2, as well as those methods discussed above for forming the recess 27 illustrated in FIG. 3. Futhermore, those modifications described above for the recesses illustrated in FIGS. 1–4 may also be incorporated in the recesses 64 of this embodiment. For example, the roughened surfaces described above for the embodiment illustrated in FIG. 3 may be incorporated in a similar recess for the dental tray 60.

As illustrated in the FIGS. 5–8, the multiple recesses 64 are formed in the outermost surface of the dental tray 60, with this outermost surface indicated generally at 66. These recesses 64 will thus deflect any light passing through the body 62 in a general inward direction. This will direct the light into the channel 68.

More particularly, the body 62 includes a base wall 70 out from which extends two substantially parallel and opposing side walls 72 and 74. These various walls 70, 72 and 74 define the channel 68. In accordance with this embodiment the side walls 72 and 74 are contoured to curve the channel 68 sufficiently to receive at least a partial arch-shaped group of a patient's teeth. Furthermore, the two side walls 72 and 74 are sufficiently separated to provide a cross-section wider than the teeth to be received in the channel 68.

The various recesses 64 are formed in the outermost surface 66 of each of the side walls 72 and 74, as well as, the base wall 70. While the embodiment illustrated in FIGS. 5–8, illustrates non-continuing multiple recesses 64 which are separately formed as three separate sections in each outermost surface 66 of each wall 70, 72 and 74, multiple, single recesses 64 can be continuously formed in the outermost surface 66 of the respective walls 70, 72 and 74.

The various recesses 64 are formed substantially parallel and contiguous to each other substantially along the length of the dental tray body 62. However, one or more of the recesses 64, such as the recess indicated at 65, may be positioned at an angle to the other recesses 64 in order to ensure that the light is substantially deflected inward to all areas of the channel 68. That is, by properly positioning the recesses 64, the light traveling through the body 62 is incrementally deflected inward to illuminate substantially the entire length of the channel 68.

Adjacent recesses 64 may be spatially separated from each other at varying distances. The precise spatial separation between adjacent recesses 64 is dependent upon the desired amount of illumination for the channel 86. This desired amount of illumination is dependent upon the light source being used, and the amount of illumination necessary to satisfactorily initiate the polymerization or curing of any material deposited in the channel 68. As will be discussed more fully herein a material is deposited in the channel 68 for the purpose of preparing a dental impression of a patient's teeth.

In order to direct light through the body 62 the dental tray 60 is further formed with at least a first primary light portal, seen generally at 76. This portal 76 is generally a flat surface against which a light source is positioned. As seen in the FIGS. 5–8 this portal 76 forms the end of a tubular conduit 78 formed in a handle 80, which handle 80 is integrally formed with and protrudes outward from the dental tray body 62.

The handle 80 is grasped by a technican during the positioning of the dental tray 60 in the mouth of a patient, and is also grasped while removing the dental tray 60.

Any suitable light source, not shown, which is receivable in the tubular conduit 78 for directing light towards the portal 76 can be used with the dental tray 60. An example of a suitable light source is disclosed in U.S.

Pat. No. 4,386,344, issued to Gonser, on May 24, 1983. The preferred amount of illumination to be provided by the selected light source is within the range of 360 to 600 nanometers.

As stated, the amount of illumination provided by the selected light source should be compatible with the amount of illumination necessary for initiating the polymerization of any material deposited in the channel 68. Further, the amount of illumination provided by the light source should also be compatible with the number of recesses 64 formed in the body 62 to provide the necessary amount of illumination in the channel 68.

In accordance with the illustrated embodiment the body 62 is further formed at the juncture between the body 62 and the handle 80 with a notch 82. In particular this notch 82 is a generally tear-shaped depression having a cross-section larger than the recesses 64, and is positioned contiguous to the end of the handle 80. The positioning and shape of the notch 82 is specifically choosen to deflect the light passing through the portal 76 down through the length of the dental tray body 62. This ensures that a maximum amount of the light will travel through the tray body 62 to impinge upon the recesses 64.

The precise position and shape of this notch 82 is dependent upon the amount of illumination being directed through the portal 76, and the amount of illumination necessary in the channel 68 to initiate the desired polymerization. For that matter, if the light source being used provides sufficient illumination there is no necessity to form the body 62 with a notch 82. That is, the selected light source may direct such a large amount of light through the portal 76, and thus through the dental tray body 62, that the channel 68 will receive an excess amount of illumination. In this case a notch 82 is not required, since this notch 82 is typically provided to ensure that a sufficient amount of light will travel through the body 62 to provide the desired degree of illumination in the channel 68.

Additionally, it may be necessary to form the dental tray body 62 with additional portals when the light source being used does not produce sufficient illumination for the channel 68. As illustrated the dental tray body 62 is integrally formed with a secondary light portal 84. This light portal 84 is positioned at the end of a secondary conduit 86 formed in a shoulder 88, which shoulder 88 extends out from the handle 80. The conduit 86 is also dimensioned to receive a suitable light source, not shown.

In the illustrated embodiment the dental tray body 62, handle 80 and shoulder 88 are integrally formed from the optically transmissive material. Furthermore the various recesses 64, and notch 82, are integrally formed in the dental tray body 62 during the initial formed process in a manner as described above for the embodiment illustrated in FIGS. 1 and 2, otherwise, the various recesses 64 and 82 may be formed in a previously formed dental tray 60 by a cutting operation as described for the embodiment illustrated in FIG. 3.

As stated the dental tray of the invention is used to prepare a dental impression of a patient's teeth using a light curable or polymerizable material. Any suitable polymeric material may be used for the purposes of the invention, with the selected material required to be flowable and be either light curable or polymerizable. That is, the polymeric material useful for the practice of the invention is either of the type which will cure upon receiving satisfactory illumination, or be of the type which is polymerized upon receiving satisfactory illumination.

A particularly useful light polymerizable material is disclosed in the above mentioned U.S. Pat. No. 4,553,936, which disclosure is incorporated herein by reference.

In accordance with the method of the invention a suitable light polymerizable or curable material is deposited in the channel 68. After such material has been deposited the dental tray 60 is positioned in a patient's mouth. A selected portion of the patient's teeth is embedded into the material. Once this has been performed a suitable light source is positioned in the conduit 78 to direct light through the portal 76. The light will enter and pass through the dental tray body 62, and will be deflected towards the material in the channel 68 by the respectively positioned recesses 64. After the necessary amount of time has lapsed the dental tray 60, with the now cured or polymerized material is removed from the patient's mouth.

If additional illumination is needed to perfect the curing or polymerization of the material the light source, or if necessary another light source, is positioned in the conduit 86 to direct light through the portal 84.

When using the polymerizable material disclosed in the incorporated reference, in conjunction with a light source providing an illumination in the range of 360 to 600 manometers, the method of preparing a dental impression may be substantially completed within about three minutes, typically within about one minute.

While the preferred embodiments have been described and illustrated, various modifications and substitutions may be made thereto without departing from the scope of he invention. Accordingly, it should be understood that the present invention has been described by way of illustration and not limitation.

What is claimed is:

1. A dental tray comprising:
   a trough shaped optically transmissive tray body characterized by substantially total internal reflection having formed therein a channel being sufficiently curved to receive at least a partial arch-shaped group of teeth, said channel having a cross-section wider than said teeth to be received therein, said tray body having an outer surface with multiple, contiguously positioned recesses, each recess being defined by two opposing surfaces which angle inwardly from said outer surface toward each other to define therebetween an included angle, and with said tray body formed with at least a first light portal upon which a light source can be directed to direct light through said optically transmissive body for reflection and refraction from the inwardly angled surfaces of the recesses toward the channel of the tray body.

2. The dental tray of claim 1 wherein said recesses are substantially triangularly shaped recesses.

3. The dental tray of claim 1 wherein said included angle is from about seventy to about one hundred ten degrees.

4. The dental tray of claim 1 wherein said included angle is from about eighty-five to about ninety-five degrees.

5. The dental tray of claim 2 wherein said included angle is from about eighty-five to about ninety-five degrees.

6. The dental tray of claim 1 wherein said channel is defined by two opposing spatially separated walls extending upwards from the remainder of said body.

7. The dental tray of claim 6 wherein said recesses are arranged along each of said body outer surfaces along said two opposing walls and said remainder of said body.

8. The dental tray of claim 1 wherein said body is formed by two opposing spatially separated walls extending upwards from and integrally formed to a base wall to define said channel.

9. The dental tray of claim 8 wherein said recesses are arranged along each of said body outer surfaces along said two opposing walls and said base wall.

10. The dental tray of claim 9 wherein said included angle is from about seventy to about one hundred ten degrees.

11. The dental tray of claim 9 wherein said included angle is from about eighty-five to about ninety-five degrees.

12. The dental tray of claim 7 wherein said recesses are formed by two opposing surfaces which angle inwardly from said body outer surface for a distance substantially equivalent to from about two to about eighty percent of the cross-sectional distance of each of said walls and of said remainder of said body.

13. The dental tray of claim 9 wherein said recesses are formed by two opposing surfaces which angle inwardly from said body outer surface for a distance substantially equivalent to from about two to about eighty percent of the cross-sectional distance of each of said walls and of said base.

14. The dental tray of claim 7 wherein said recesses are formed by two opposing surfaces which angle inwardly from said body outer surface for a distance substantially equivalent to from about two to about twenty-six percent of the cross-sectional distance of each of said walls and of said remainder of said body.

15. The dental tray of claim 9 wherein said recesses are formed by two opposing surfaces which angle inwardly from said body outer surface for a distance substantially equivalent to from about two to about twenty-six percent of the cross-sectional distance of each of said walls and of said base.

16. The dental tray of claim 7 wherein said recesses are formed by two opposing surfaces which angle inwardly from said body outer surface for a distance substantially equivalent to from about two to about sixteen percent of the cross-sectional distance of each of said walls and of said remainder of said body.

17. The dental tray of claim 9 wherein said recesses are formed by two opposing surfaces which angle inwardly from said body outer surface for a distance substantially equivalent to from about two to about sixteen percent of the cross-sectional distance of each of said walls and of said base.

18. The dental tray of claim 17 wherein said included angle is from about seventy to about one hundred ten degrees.

19. The dental tray of claim 17 wherein said included angle is from about eighty-five to about ninety-five degrees.

20. The dental tray of claim 18 wherein at least a first surface of each of said recesses is roughened.

21. The dental tray of claim 9 11 17 further being formed with an integral handle, which handle extends outward from said body and is formed with a tubular passageway therethrough, said passageway being dimensioned to receive a source of illumination and which passageway is formed with an innermost end which functions as said portal.

22. The dental tray of claim 11 further being formed with an integral handle, which handle extends outward from said body and is formed with a tubular passageway therethrough, said passageway being dimensioned to receive a source of illumination and which passageway is formed with an innermost end which functions as said portal.

23. The dental tray of claim 17 further being formed with an integral handle, which handle extends outward from said body and is formed with a tubular passageway therethrough, said passageway being dimensioned to receive a source of illumination and which passageway is formed with an innermost end which functions as said portal.

* * * * *